United States Patent
Van Krieken et al.

(10) Patent No.: US 9,249,073 B2
(45) Date of Patent: Feb. 2, 2016

(54) METHOD FOR MANUFACTURING SUCCINIC ACID ESTERS

(71) Applicant: PURAC BIOCHEM BV, Gorinchem (NL)

(72) Inventors: Jan Van Krieken, Gorinchem (NL); André Banier De Haan, Gorinchem (NL); Jan Van Breugel, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 14/767,021

(22) PCT Filed: Feb. 13, 2014

(86) PCT No.: PCT/EP2014/052825
§ 371 (c)(1),
(2) Date: Aug. 11, 2015

(87) PCT Pub. No.: WO2014/125027
PCT Pub. Date: Aug. 21, 2014

(65) Prior Publication Data
US 2015/0368170 A1    Dec. 24, 2015

Related U.S. Application Data

(60) Provisional application No. 61/764,628, filed on Feb. 14, 2013.

(30) Foreign Application Priority Data

Feb. 14, 2013  (EP) ..................................... 13155241

(51) Int. Cl.
C07C 67/38    (2006.01)
C07C 67/08    (2006.01)
C07C 29/149   (2006.01)
C07C 29/09    (2006.01)

(52) U.S. Cl.
CPC ............... C07C 29/095 (2013.01); C07C 67/08 (2013.01); C07C 67/38 (2013.01); C07C 29/149 (2013.01)

(58) Field of Classification Search
CPC ........ C07C 67/38; C07C 67/08; C07C 29/149
USPC .......................................... 560/204; 568/864
See application file for complete search history.

(56) References Cited

U.S. PATENT DOCUMENTS 2,844,619 A * 7/1958 Escobar .................. C07F 9/025
                                                 558/149
4,801,448 A * 1/1989 Wilson .................... A01N 25/18
                                                 424/84
4,818,526 A * 4/1989 Wilson .................... A01N 41/12
                                                 424/84

* cited by examiner

*Primary Examiner* — Elvis O Price
(74) *Attorney, Agent, or Firm* — Harris A. Pitlick (57) ABSTRACT

The invention pertains to a process for preparing a succinic acid ester comprising the steps of bringing an aqueous liquid comprising succinic acid, alcohol, and at least 5 wt. % of a dissolved chloride salt selected from magnesium chloride, calcium chloride, and zinc chloride, calculated on the weight of the liquid, to reaction conditions, thereby obtaining a succinic acid ester, and recovering the succinic acid ester and an aqueous solution comprising the dissolved chloride salt. It has been found that the process according to the invention shows a high yield and has a high reaction rate. Additionally, it has been found that the process makes it possible to carry out the separation of the succinic acid ester from the aqueous reaction medium in high yield.

14 Claims, 7 Drawing Sheets

Figure 4:
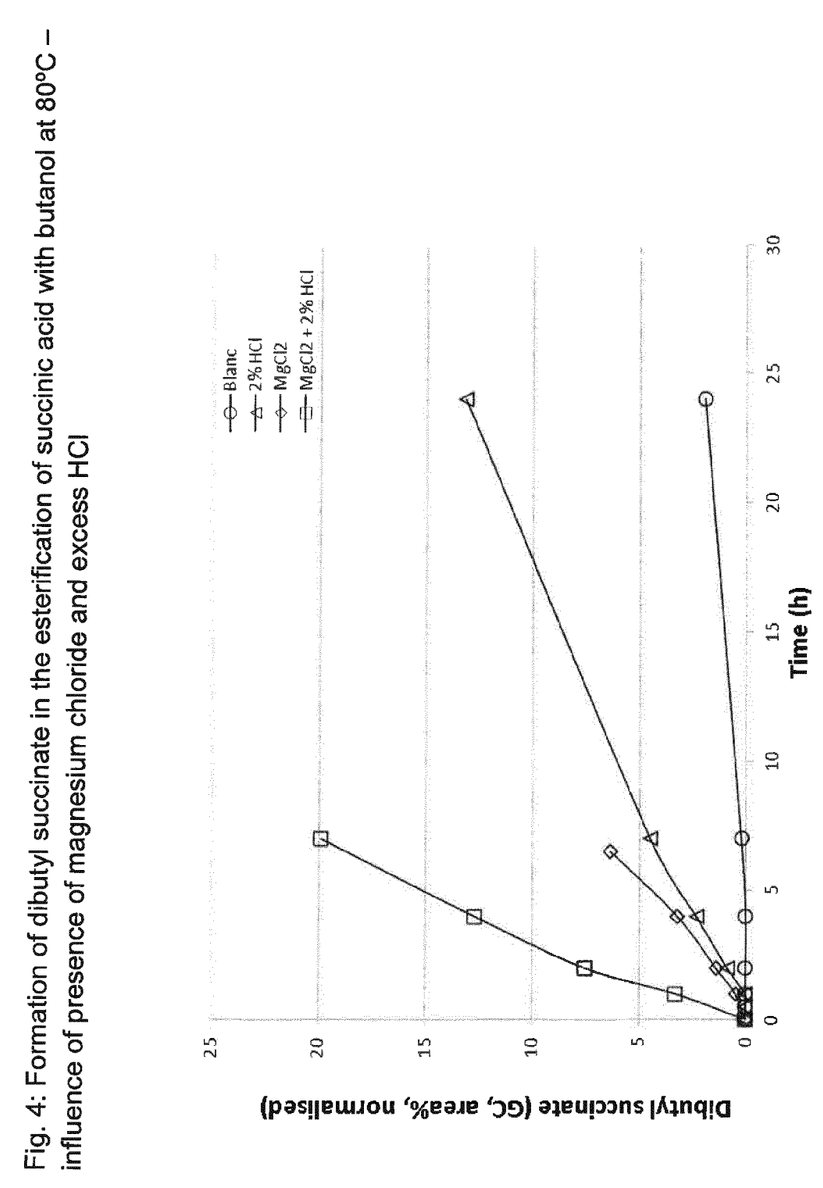

Fig. 4: Formation of dibutyl succinate in the esterification of succinic acid with butanol at 80°C – influence of presence of magnesium chloride and excess HCl Fig. 5: Formation of dibutyl succinate in the esterification of succinic acid with butanol in the presence of magnesium chloride – influence of concentration and presence of excess HCl

METHOD FOR MANUFACTURING SUCCINIC ACID ESTERS

The present invention is directed to a method for preparing succinic acid esters. The invention also pertains to a method for manufacturing 1,4-butane diol.

Succinic acid esters find application in numerous uses. They can, e.g., be used as solvents, monomers for polymer production, and intermediate for chemicals production.

Succinic acid esters have been found particularly attractive as starting material for the production of butane diol.

1,4-Butanediol is used industrially as a solvent and as starting material in the manufacture of various types of chemicals, e.g., in the manufacture of some types of plastics, elastic fibers and polyurethanes. It can be converted to tetrahydrofuran or butyrolactone, which are useful intermediates in their own right. Butane diol is currently generally produced from petrochemical precursors, primarily acetylene. In view of the large volumes in which it is used, there is interest in the manufacture of butanediol from renewable resources. Succinic acid esters, which can be derived from succinic acid, which can be manufactured from renewable resources, are therefore an attractive starting material.

It will be evident that for succinic acid esters to be commercially viable as starting material, it will be necessary to manufacture succinic acid by a process which is cost-effective and efficient. The present invention provides such a process.

The present invention therefore pertains to a process for preparing a succinic acid ester comprising the steps of bringing an aqueous liquid comprising succinic acid, alcohol, and at least 5 wt. % of a dissolved chloride salt selected from magnesium chloride, calcium chloride, and zinc chloride, calculated on the weight of the liquid, to reaction conditions, thereby obtaining a succinic acid ester, and recovering the succinic acid ester and an aqueous solution comprising the dissolved chloride salt.

Succinic acid is a di-acid, and therefore allows the formation of mono-esters and di-esters. While both can be formed with the process according to the invention, the invention is directed in particular to the formation of di-esters.

It has been found that the process according to the invention shows a high yield and has a high reaction rate. Additionally, it has been found that the process makes it possible to carry out the separation of the succinic acid ester from the aqueous reaction medium in high yield.

More specifically, it has been found that the presence of a dissolved chloride salt selected from magnesium chloride, calcium chloride, and zinc chloride in the reaction mixture leads to an increase in reaction rate and product yield as compared to the situation where the specified salt is absent. Further, it has been found that the presence of at least 5 wt. % of these salts may improve the separation of the ester from the aqueous medium, in particular where the separation takes place via phase separation or extraction.

It has been found that the process according to the invention also has a number of advantages also as compared to a process wherein in a first step succinic acid is manufactured and separated from a salt solution, and esterification takes place in a second step. In the process according to the invention, where the esterification takes place in the presence of the salt, it is not necessary to submit the acid to a purification step. Therewith, the total purification efforts of the acid and the ester are reduced, even when the purification of the acid is taken into account. Further, as indicated above, the presence of the salt improves the separation process. In consequence, the process according to the invention can be carried out at higher water contents than separation of ester in the absence of salt, or separation of succinic acid from an aqueous solution. Therewith, less water has to be removed, and this is an economic advantage. Further advantages of the present invention and specific embodiments thereof will become clear from the further specification.

Not wishing to be bound by theory, it is believed that the presence of a dissolved chloride salt selected from magnesium chloride, calcium chloride, and zinc chloride in the reaction mixture leads to a decrease in pH, which results in an increase in reaction rate. It is further believed that the presence of at least 5 wt. % of a dissolved chloride salt selected from magnesium chloride, calcium chloride, and zinc chloride leads to improved phase separation and extraction processes.

The process according to the invention starts out with an aqueous liquid comprising succinic acid, alcohol, and at least 5 wt. % of a dissolved chloride salt selected from magnesium chloride, calcium chloride, and zinc chloride, calculated on the weight of the liquid.

It is noted that the aqueous liquid may be a single phase solution. However, depending on the nature and amount of the acid, the alcohol, and the salt, and whether or not an extractant is present, as will be discussed in more detail below, the aqueous liquid may also be a two-phase system (comprising two liquid phases), and/or comprise solid components, e.g., acid particles.

The succinic acid concentration in the aqueous liquid may vary in wide ranges, depending, int. al., on the solubility of the acid in the liquid. As a maximum value, a value of 40 wt. % may be mentioned. As a minimum, a value of 1 wt. % may be mentioned. Below that value, economic operation may be difficult. The aqueous liquid may be a solution or a suspension. In general, the use of solutions is preferred. Therefore, in one embodiment the acid concentration is the solubility of the acid in the aqueous liquid or lower. If so desired, the temperature of the aqueous liquid may be increased to increase the solubility of the acid.

The aqueous liquid also comprises an alcohol which is to react with the acid to provide the ester. The alcohol may be any alkanol suitable for use in an esterification reaction. For example, the alcohol may be an alkanol comprising 1-8 carbon atoms. It may, for example, be selected from the group consisting of methanol, ethanol, propanol, isopropanol, butanol, pentanol, hexanol heptanol, 2-ethylhexanol, and 1-octanol. Secondary and tertiary alcohols may be used, but primary alcohols may be preferred, depending on the product to be obtained. The process works best if the alcohol has at least some solubility in the reaction mixture. The solubility of the alcohol in the reaction mixture may be increased by increasing the temperature.

The use of C1-C8 alcohol is considered preferred, with the use of C1-C4 alcohol being more preferred. Methanol, ethanol, and butanol may be used in particular.

The amount of alcohol that is present in the aqueous liquid is determined by the amount of succinic acid present in the system. The molar ratio of carboxylic acid group to be esterified to alcohol generally is in the range of 1:1 to 1:10, preferably in the range of 1:1 to 1:5.

In addition to acid and alcohol the aqueous liquid comprises at least 5 wt. % of a dissolved chloride salt selected from magnesium chloride, calcium chloride, and zinc chloride, calculated on the weight of the liquid. If the amount of dissolved salt is below 5 wt. % the advantageous effect of the present invention will not be obtained. The maximum for the amount of chloride salt is not critical to the process according to the invention. As a general value, a maximum of 40 wt. % may be mentioned. It may be preferred for the aqueous liquid to comprise 10-30 wt. % of dissolved chloride salt, in particular 15 to 25 wt. %. The chloride salt may be selected from magnesium chloride, calcium chloride, and zinc chloride. Mixtures of salts may also be applied. The use of magnesium chloride is considered preferred, because it is believed to be particularly effective in ensuring a high separation efficiency, and possibly an increased reaction rate. Additionally, the use of magnesium chloride allows for an attractive integrated process by using a thermal decomposition step. This will be discussed in more detail below.

The aqueous liquid comprising succinic acid, alcohol, and chloride salt may be obtained in various manners. In one embodiment, the succinic acid, alcohol, and chloride salt are combined in water. However, there are a number of particularly attractive possibilities.

In one embodiment, the aqueous liquid comprising succinic acid, alcohol, and chloride salt is obtained by the steps of providing an aqueous liquid comprising a magnesium-, calcium-, or zinc-salt of a succinic acid, acidifying the aqueous liquid by the addition of HCl, and adding the alcohol before, after, or simultaneous with the addition of HCl. The acidification step results in the conversion of the succinate salt into succinic acid, with simultaneous formation of the corresponding chloride salt. By selecting the concentration of succinate and HCl, a liquid may be obtained comprising the succinic acid and the chloride salt in the ranges indicated above.

If so desired the concentration of these components may be increased in various manners, e.g., by adding succinic acid or chloride salt, or by performing a concentration step, wherein water is removed from the system.

It has been found that the presence of HCl further increases the reaction rate. Therefore, in one embodiment the reaction mixture comprises additional HCl, e.g., in an amount of 0.5 to 5 wt. %, calculated on the amount of succinic acid. While HCl may be added separately to the reaction mixture, in one embodiment of the invention the acidification process is carried out using an excess of HCl as compared to the amount of HCl necessary for neutralisation of the succinate salt. In this embodiment the excess amount of HCl added may, e.g., be in an amount of 0.5 to 5 wt. %, calculated on the amount of HCl needed to convert the succinate salt into succinic acid.

The aqueous liquid comprising acid, alcohol, and chloride salt is brought to reaction conditions, thereby obtaining a succinic acid ester.

Reaction conditions generally include a temperature in the range of 20-150° C., in particular in the range of 30 to 130° C., more in particular in the range of 50 to 100° C.

The pressure during the reaction is not critical, as long as the aqueous liquid remains in the liquid form. Generally, the reaction will be carried out at a pressure of 1-5 bar, preferably under atmospheric conditions.

The step of bringing the aqueous liquid comprising acid, alcohol, and magnesium chloride to reaction conditions, thereby obtaining a succinic acid ester, can be carried out on the final liquid. It can, however, also be carried out on the liquid during formation, e.g., during an acidification reaction discussed above. In the same way, the separation step discussed below can be carried out after the esterification reaction has been completed, but also during the esterification step, or in some embodiments during the combined acidification/esterification step. Various embodiments are discussed below.

The next step in the process according to the invention, which, as indicated above may be carried out in combination with previous steps, is recovering the succinic acid ester and an aqueous solution comprising a chloride salt selected from calcium chloride, magnesium chloride, and zinc chloride. There are various ways in which this can be effected, depending on the properties of the ester.

It has been found that for certain succinate esters the product mixture may form a two-phase system, wherein the ester and chloride salt solution form separate liquid layers. This applies in particular for succinic esters of higher alcohols, say C2 and higher, in particular C3 and higher, more in particular C4 and higher, e.g., dibutyl succinate. In addition to the nature of the succinic acid ester, whether or not a two phase system will be formed will also depend on the salt concentration of the medium, with higher salt concentrations promoting the formation of a two-phase system, and on the ester concentration, with higher salt concentrations promoting the formation of a two-phase system.

The system will generally comprise excess alcohol, which, dependent on the properties of the alcohol may be present in the water layer and/or the organic layer. As soon as any ester is formed, phase-separation of the product mixture may start to occur. Since the product is effectively removed from the reaction mixture by forming a separate layer, phase-separation results in an increased esterification rate. Furthermore, phase-separation may allow for the isolation of relatively pure ester by separating the layers from each other. It should be noted that the presence of high concentrations of chloride salts improves the phase separation. Therewith, esters which do not show phase separation in mixtures with water may still show phase separation in the salt-containing system according to the invention.

The term "two-phase system" refers to a system wherein two liquid layers are present, which layers are immiscible with each other. The two-phase system comprises a liquid organic layer comprising the ester (product layer) and an aqueous layer comprising dissolved chloride salt. It is preferred for at least 80% of the carboxylate ester present in the system to be present in the liquid organic layer, in particular at least 90%, more in particular at least 95%, still more in particular at least 98%. The liquid organic layer typically comprises less than 20 wt. % of water, more in particular less than 10 wt. % of water, still more in particular less than 5 wt. % of water.

Efficient separation between the ester in the organic phase and the aqueous phase can e.g. be obtained by performing multistage countercurrent operation.

The aqueous layer comprises dissolved chloride salt as described above, and preferably less than 5 wt. % of succinic acid ester, more preferably less than 2 wt. % of succinic acid ester, and even more preferably less than 1 wt. % of succinic acid ester.

The aqueous layer preferably contains less than 5 wt. % of the total amount of succinic acid provided to the system, more preferably less than 2 wt. %, still more preferably less than 1 wt. %.

The process according to the invention generally shows a conversion of at least 90%, expressed as the amount of succinic acid converted, calculated on the amount of succinic acid originally provided to the system. Preferably the conversion is at least 95%, more preferably at least 99%.

The process according to the invention can be operated to a yield of at least 90%, expressed as the amount of ester resulting from the process calculated on the theoretical yield, calculated from the amount of acid originally provided to the system. Preferably the yield is at least 95%, more preferably at least 98%, still more preferably at least 99%. It has been found that the process according to the invention can give such high yields, especially when it is ensured that proper recycling steps are incorporated into the process design.

In one embodiment of the present invention, an extraction agent is used to separate the ester from the magnesium chloride solution, which extraction agent, also indicated as extractant, is substantially not miscible with water. This method may be attractive if the solubility of the ester in water is such that phase separation will not occur, or will occur only to a limited extent. This applies to dimethyl succinate and to diethyl succinate, depending on the conditions. In this case, the use of an extractant improves the separation of the ester from the aqueous liquid.

The use of an extractant results in the formation of a two-phase system which comprises a liquid organic layer comprising the extraction agent and the ester (product layer) and an aqueous layer comprising dissolved chloride salt. The system will generally comprise an excess alcohol, which, dependent on the properties of the alcohol and the extractant, may be present in the water layer and/or the organic layer.

The extraction agent may be added when the esterification reaction has been completed. It is also possible for the extraction agent to be present during the esterification reaction. This may or may not be attractive, as will be explained below. The esterification reaction of succinic acid is a two-step reaction, wherein first one carboxylic acid group is esterified to form succinic acid mono-ester, after which the second carboxylic acid group is esterified to form the succinic acid diester. Where an extractant is present, it may be that the succinic acid mono-ester is preferentially taken up in the extractant. If the alcohol remains in the aqueous phase, this may limit the conversion of the succinic acid mono-ester into the di-ester. Whether or not this effect occurs will depend on the nature of the extractant and the nature of the alcohol. It is within the scope of the skilled person to investigate this effect for a particular combination of alcohol and extractant using routine experimentation. Nevertheless, where an extractant is used, it may be preferred to add it to the reaction medium after the esterification reaction has been completed.

Examples of suitable extractants are aliphatic and aromatic hydrocarbons, such as alkanes and aromatic compounds, ketones, and ethers. Mixtures of various compounds may also be used.

Examples of suitable aliphatic alkanes are C5-C10 straight chain, branched, or cyclic alkanes, e.g., octane, hexane, cyclohexane, 2-ethyl-hexane, and heptane.

Examples of suitable aromatic compounds are C6-C10 aromatic compounds, e.g., toluene, xylenes, and ethylbenzene.

Examples of suitable ketones are C5+ ketones, more in particular C5-C8 ketones in the present invention. C5+ stands for ketones with at least 5 carbon atoms. The use of C9+ ketones is less preferred. The use of methyl-isobutyl-ketone (MIBK) has been found to be particularly attractive.

Examples of suitable ethers are C3-C6 ethers, e.g., methyl tert-butyl ether (MTBE) and diethyl ether (DEE).

The amount of extractant used in the present invention is generally not critical. The minimum amount will be determined by the amount necessary to ensure an effective separation process. The maximum amount will be determined by commercial operation, where the addition of further extractant does not lead to an improved separation, but only leads to increased reactor volume. As a general range, a volume ratio of (water+succinic acid+alcohol+salt+ester):extractant within the range of 1:0.01 to 1:10, in particular 1:0.1 to 1:10 may be mentioned. For the distribution of succinic acid ester, succinic acid, alcohol, and water over the two phases, reference is made to what is stated above for the phase separation process.

Whether or not the addition of an extractant is desired will depend on the nature of the succinic acid ester and on the further conditions like salt concentration, acid concentration, alcohol concentration, and ester concentration. Where the succinic acid ester is in itself not miscible with water or the chloride salt solution, phase separation will occur spontaneously, and the addition of an extractant is not necessary. This is in particular the case where the succinic acid ester is an ester of succinic acid with an alcohol with at least two carbon atoms, in particular at least three carbon atoms, more in particular at least four carbon atoms. In this case, it may be preferred not to add an extractant to prevent the addition of unnecessary compounds. However, if so desired, an extractant can be added in this case, and it may sometimes be attractive to do so to increase the adsorption of the ester in the organic phase by altering the distribution coefficient. Where the succinic acid ester is miscible with the salt solution, e.g., in the case of dimethyl succinate, it will be necessary to add an extractant if recovery of the ester through phase separation is desired. For diethyl succinate the use of an extractant may also be attractive.

As indicated above, the presence of dissolved chloride salt during the esterification reaction leads to an increase in reaction rate. It was further found that the presence of dissolved chloride salt may promote and/or enhance separation of the ester by phase separation or extraction. More specifically, an increase in the concentration of dissolved chloride salt may lead to a higher distribution coefficient of the ester between the organic layer and the aqueous layer, resulting in an improved ester yield and a lower organic content of the aqueous layer. Further, in some cases phase separation will only take place at higher concentrations of dissolved chloride salt. Therefore, where the ester is to be separated from the chloride salt solution by a process comprising phase separation or extraction it is preferred for the chloride salt solution to have a relatively high concentration. In this embodiment it may be preferred for the chloride salt concentration in the aqueous liquid to be at least 10 wt. %, more preferably at least 15 wt. %, even more preferably at least 20 wt. %.

Where the ester is separated from the chloride salt solution by a step comprising phase separation or extraction, separation of the different layers can be carried out by methods known in the art for liquid-liquid separation. Examples of suitable apparatus and methods for liquid-liquid separation include decantation, settling, centrifugation, use of plate separators, use of coalescers, and use of hydrocyclones. Combination of different methods and apparatus may also be used.

The method of the invention may further comprise a water removal step prior to or during esterification. For example, water may be removed before adding the alcohol, but after adding the hydrogen chloride. Such a step may allow for a higher concentration of chloride salt and/or a higher concentration of succinate. This may increase the esterification reaction rate and/or enhance phase-separation. Preferred succinate concentrations to which can be concentrated are mentioned above for the aqueous mixture. An upper limit may be derived from the solubility of chloride salt in the solution, as the presence of precipitated salt does not provide additional advantages, but may result in processing issues.

As indicated above, it is preferred for the chloride salt used in the present invention to be magnesium chloride. One reason why this salt is preferred is that it allows an attractive method of processing for the chloride salt solution, namely by thermal decomposition. Therefore, in one embodiment of the present invention, the magnesium chloride solution resulting from the separation step is provided to a thermal decomposition step, where it is converted into magnesium oxide and hydrogen chloride. The process of thermal decomposition is also known under the terms thermal hydrolysis and thermohydrolysis.

Thermal decomposition is generally conducted at a temperature of a least 300° C. Preferably, thermal decomposition is conducted at a temperature of at least 350° C. Due to energy costs, the temperature is preferably below 1000° C., more preferably below 800° C. For example, the temperature at which thermal decomposition is conducted may be 350-600 or 400-450° C.

Preferably, the magnesium chloride solution has a magnesium chloride concentration of 15-40 wt. %, more preferably 25-35 wt. %. Too high amounts of magnesium chloride present in the solution may result in precipitation of magnesium chloride upon entering the thermohydrolysis unit. Water may be added to or removed from the hydrogen chloride solution recovered in the method of the invention in order to obtain a desirable magnesium chloride concentration.

Suitable apparatuses for conducting thermal decomposition are known in the art. For example, a spray roaster or a fluid bed roaster can be used. Such apparatuses can for example be obtained at SMS Siemag, Andritz. Tenova, CMI, and Chemline.

The magnesium oxide obtained in thermal decomposition will be in solid form. It can, if so desired, be recycled for use in a fermentation process, in particular as a neutralizing agent. The MgO can be used directly, but it is also possible to convert it to magnesium hydroxide by reaction with water. The hydrogen chloride obtained in the thermal decomposition may, if so desired, be used in an acidification step.

The method may further comprise a fermentation step, wherein an aqueous feed comprising a succinate salt is formed. Such a step typically comprises the substeps of fermenting a carbon source by means of a micro-organism to form a fermentation medium comprising succinic acid, and (partially) neutralizing the fermentation medium in order to establish a desirable pH by adding a neutralizing agent, in this case preferably a calcium base, a zinc base, or a magnesium base, more in particular a magnesium base, to form the succinate salt. Subsequently, biomass may, if so desired, be separated from the fermentation medium, for example by (ultra) filtration, centrifugation or decantation of the biomass or by precipitation of the succinate salt (typically magnesium succinate) from the fermentation medium. As described above, magnesium oxide obtained in the thermal decomposition step can be recycled in the precipitation step as a neutralizing agent or precursor thereof.

In one embodiment the process according the invention comprises the further step of reacting the succinic acid ester with hydrogen in the presence of a catalyst to form 1,4-butane diol. The reaction can, e.g., take place at a temperature in the range of 180-300° C., and a pressure of 1-40 bar. The hydrogen to feed molar ratio may, e.g., be in the range of 10:1 to 400:1. The catalyst may be a hydrogenation catalyst known in the art, comprising a hydrogenation metal, e.g., one or more metals of group 6, 7, 8, 9, 10, or 11 of the Periodic Table of elements. The use of zinc, copper, chromium, palladium, or ruthenium may be preferred, while the use of a combination of zinc and copper or a combination of copper and chromium may be particularly attractive.

Figure 1:
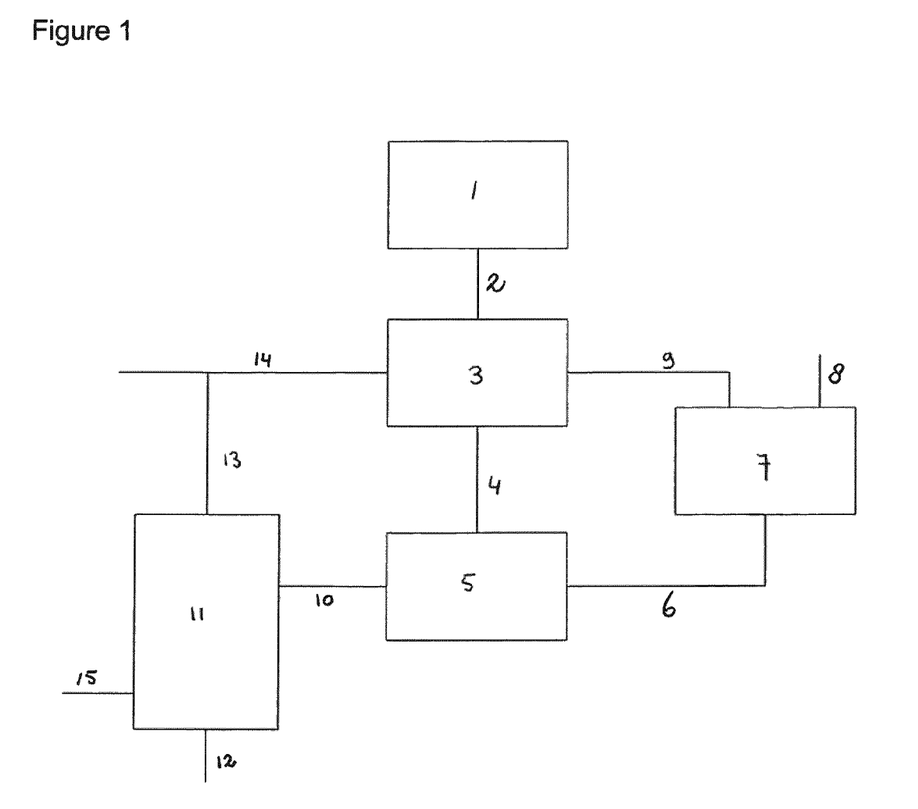

FIG. 1 illustrates the process according to the invention embedded in an integrated process. A fermentation process is carried out in fermentation reactor (1) generating succinic acid. A base is added during fermentation (not shown), resulting in the formation of a succinate salt. The base preferably is a calcium base, e.g. calcium oxide, hydroxide, or carbonate, a magnesium base, e.g., magnesium oxide, hydroxide or carbonate, or a zinc base, e.g., zinc oxide, hydroxide, or carbonate. The use of a magnesium base is preferred. A product stream (2) comprising a succinate salt, preferably calcium succinate, magnesium succinate, or zinc succinate, in particular magnesium succinate, is withdrawn from the fermentation reactor, and provided to an acidification/esterification reactor. If so desired, intermediate purification steps such as biomass removal may be carried out in manners known in the art. In acidification/esterification reactor (3), alcohol is added through line (14), and hydrogen chloride is added through line (9). The hydrogen chloride may be in the gas phase or in solution in water. The hydrogen chloride may be added prior to the addition of alcohol, simultaneous with the addition of alcohol, or after the addition of alcohol. The reactor is brought to esterification conditions. Next, a separation step is carried out. In the figure, this is presented as a separate step (5), but it may be carried out in the esterification reactor. The separation step (5) yields an aqueous stream (6), which comprises the chloride salt. If the chloride salt is magnesium chloride, stream (6) can be provided to a thermal decomposition step (7), where the aqueous magnesium chloride solution is decomposed to form magnesium oxide, removed through line (8), and hydrogen chloride, removed through line (9). The hydrogen chloride may be recycled to the acidification step as illustrated in the figure, either as gas, or after having been absorbed in an aqueous liquid to form a solution. The magnesium oxide may be recycled to the fermentation step (1) (not shown), either directly or after conversion into magnesium hydroxide or carbonate. The product stream (10) removed from the separation step (5) comprises the succinic ester product. It will generally also comprise alcohol, as the esterification reaction is generally carried out in the presence of a surplus of alcohol. The product stream (10) may be provided to a separation step (11), where the alcohol is separated from the succinic acid ester. The separation step may, e.g., be a distillation step. The separation step yields a product stream (12) comprising the succinic acid ester, and an alcohol stream (13), which can be provided to the alcohol feed (14). There may be a bottom stream (15) which may contain succinic acid and optional condensation products. This stream, if present, may be recycled to the esterification step, or otherwise disposed of.

Figure 2:
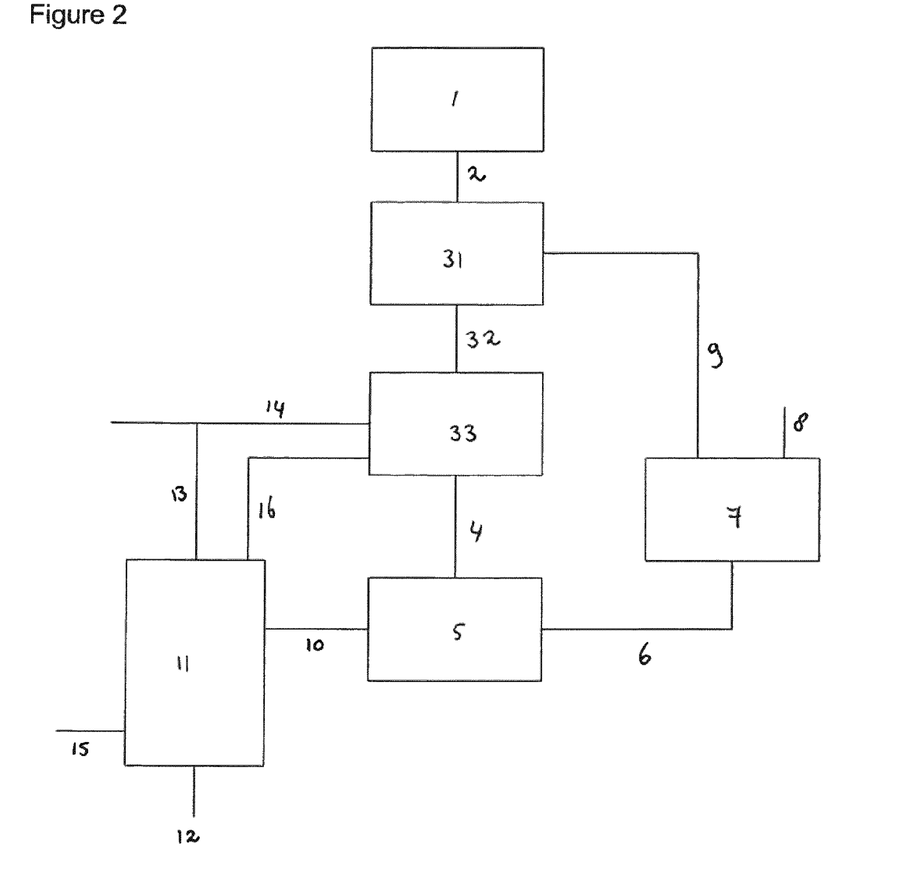

FIG. 2 provides a variation on the process of FIG. 1. In the process of FIG. 2) an extractant is added to the separation step (5) through line (16). The product stream (10) comprises succinic acid ester, alcohol, and extractant. In this case, separation step (11) yield an alcohol stream (13), an ester stream (12), and a recycle extractant stream (16) which is provided to esterification reactor (33). Separation step (11) may, e.g., be carried out by fractional distillation. Further, in the process of FIG. 2 the acidification step and the esterification step are separated, with the acidification step being carried out in acidification reactor (31), to which hydrochloric acid is provided through line (9). The acidified product, which is an aqueous liquid comprising succinic acid and chloride salt is provided through line (32) to esterification reactor (33) to which alcohol is provided through line (14).

The extractant stream can be provided to the esterification reactor when the esterification reaction has been completed, or before or during the reaction. As discussed above, it may be preferred for the extractant to be added when the esterification reaction has been completed.

In one embodiment of the present invention, the esterification step and the separation step are combined in a single step in a single reactor. In one embodiment, this reactor is operated in countercurrent operation, wherein the succinic acid is provided to the top of the reactor in a solution comprising a chloride salt as described above. Alcohol is provided to the bottom of the reactor. The succinic acid ester is withdrawn from the top of the reactor. An aqueous solution comprising the dissolved chloride salt is withdrawn from the bottom of the reactor. This embodiment can also be carried out in the presence of an extractant. In this case, the extractant is provided to the bottom of the reactor. This may be done in various manners, e.g., separately, or combined with the alcohol. The extractant is withdrawn from the top of the reactor in admixture with the succinic acid ester. It has been found that this embodiment allows obtaining a high conversion in combination with a high yield, as described above. This embodiment is illustrated in FIG. 3, without being limited thereto or thereby.

Figure 3:
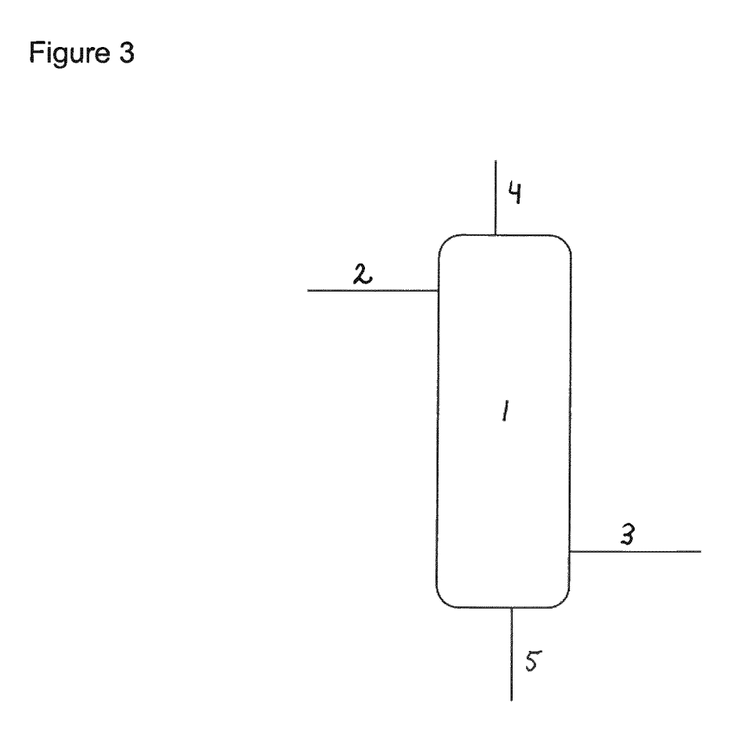

FIG. 3 shows a reactor (1) provided with an inlet (2) at the top, wherein an aqueous liquid, e.g., a solution comprising succinic acid and soluble is provided to the reactor. Alcohol, and if so desired extractant, are provided to the bottom of the reactor through line 3. The reactor is at esterification conditions discussed above. A top stream is withdrawn from the reactor through line (4). The top stream comprises succinic acid ester, and if present extractant. A bottom stream comprising the chloride salt is withdrawn through line (5). For information on the components in the various liquids, processing conditions, and processing of the resulting products reference is made to the general description above.

It will be evident to the skilled person that the various aspects of the present invention which are described above in different paragraphs may be combined.

While the figures illustrate various integrated processes, it is within the scope of the skilled person to combine the various elements of the process in suitable manners.

The invention and certain embodiments of the inventions are illustrated by the following examples and/or embodiments, without being limited thereto or thereby.

EXAMPLE 1

Esterification of Succinic Acid with Butanol—Comparison with Systems not Containing Magnesium Chloride Jacketed glass vessels, heated by a thermostatic water bath to 80° C., were charged with succinic acid, water, 1-butanol, optionally magnesium chloride, and optionally HCl. The butanol was added at t=0 and magnetic stirring was applied.

The succinic acid concentration in the aqueous phase was 14.2%. The molar ratio of succinic acid:BuOH was 1:4. In experiment 2 and 4 an amount of HCl simulating a 2% of HCl excess during acidulation was added. The composition of the samples at t=0 is given in the following table.

TABLE 1

| Mixture | Succinic acid (g) | MgCl$_2$•6H$_2$O (g) | Butanol (g) | Water (g) | HCl 20 w % (g) |
|---------|-------------------|----------------------|-------------|-----------|----------------|
| 1 | 4.97 | — | 12.48 | 30.03 | — |
| 2 | 4.97 | — | 12.48 | 30.03 | 0.31 |
| 3 | 5.01 | 8.61 | 12.60 | 21.96 | — |
| 4 | 5.01 | 8.64 | 12.70 | 21.60 | 0.33 |

During the experiments in time samples will be taken at t=0, 0.5, 1, 2, 4, 7 and 24 h. Four drops of the mixture of the upper layer were diluted in 1.5 ml solvent (acetone or methanol) before the samples are analysed by GLC (area %).

The results are given in FIG. 4. As can be seen from this Figure, Mixture 1, which contains no magnesium chloride or HCl shows the lowest reaction rate. The reaction rate can be improved by adding HCl (Mixture 2) or magnesium chloride (Mixture 3). Best results are obtained when a combination of magnesium chloride and HCl is used (Mixture 4).

EXAMPLE 2

Esterification of Succinic Acid with Butanol, in the Presence of Magnesium Chloride—Variation in Concentration, Presence of HCl Four mixtures of succinic acid, magnesium chloride, butanol and water were prepared. To two of them a small amount of hydrochloric acid was added. The composition of the four mixtures is shown in Table 2.

TABLE 2

| Mixture | Succinic acid (g) | MgCl$_2$•6H$_2$O (g) | Butanol (g) | Water (g) | HCl 20 w % (g) |
|---------|-------------------|----------------------|-------------|-----------|----------------|
| 1 | 5.01 | 8.61 | 12.60 | 21.96 | — |
| 2 | 10.02 | 17.23 | 25.43 | 12.94 | — |
| 3 | 5.01 | 8.64 | 12.7 | 21.6 | 0.33 |
| 4 | 10.06 | 17.33 | 25.27 | 12.85 | 0.64 |

Mixture 1 represents the result of an acidulation of a 30 wt. % magnesium succinate solution with a 20 wt. % HCl solution in a HCl/MgSuc molar ratio of 2.00:1.00.

Mixture 2 is similar to mixture 1, but with only half the amount of water present, as could for example be obtained by a water removal step prior to or during esterification.

Mixture 3 represents the result of an acidulation of a 30 wt. % magnesium succinate solution with a 20 wt. % HCl solution, in a 2.04:1.00 molar ratio. This ratio corresponds with a 2% of HCl excess during acidulation.

Mixture 4 is similar to mixture 3, but with only half the amount of water present, as could for example be obtained by a water removal step prior to or during esterification.

The molar ratio of butanol:succinic acid in all mixtures was 4.0:1.0, which corresponds to a 100% of excess of the theoretical amount for the complete esterification of succinic acid with butanol.

Figure 5:
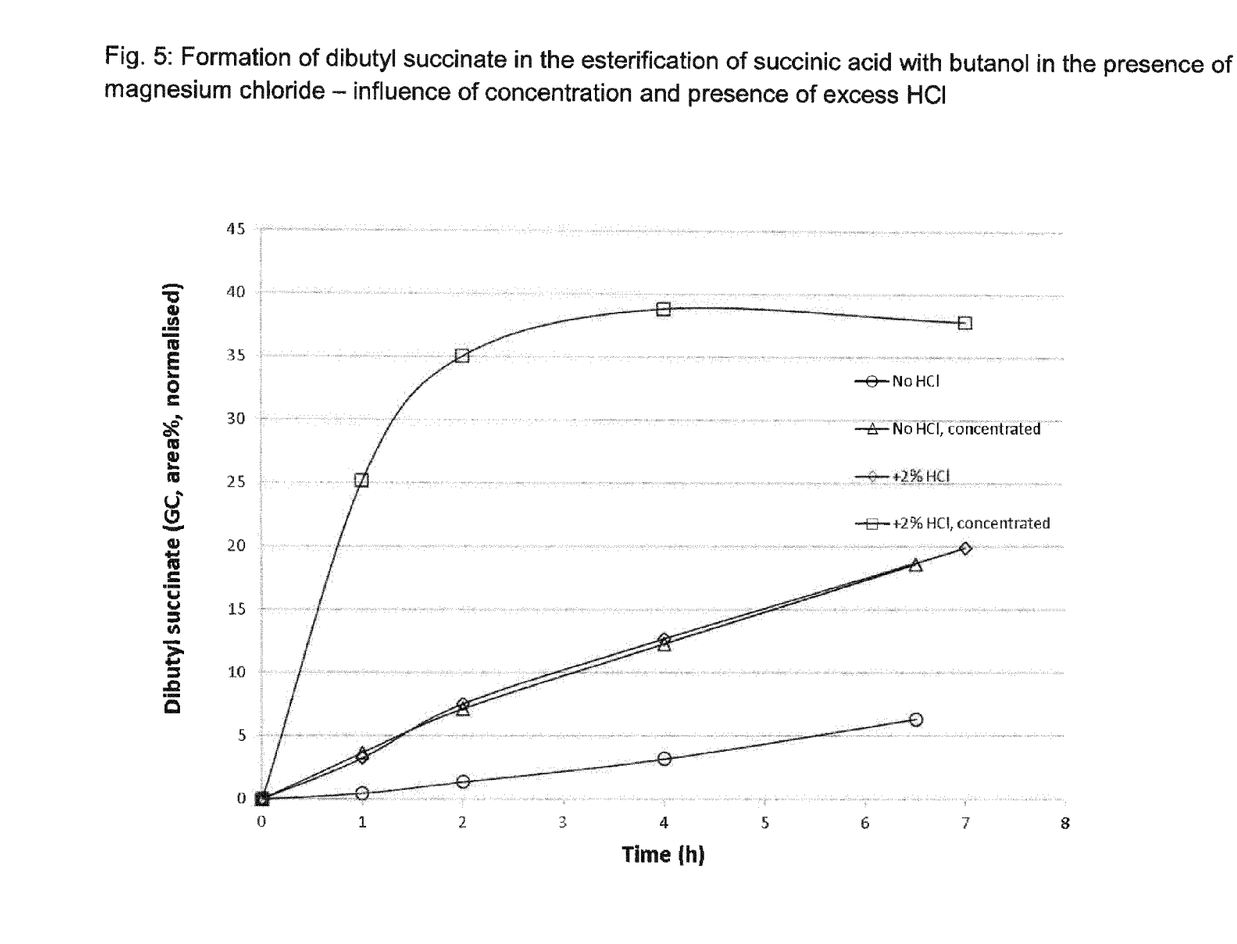

Each mixture was reacted in a vessel for 7 hours under magnetic stirring at a temperature of 80° C. After 1, 2, 4 and 6.5/7 hours the stirrer was stopped. Stopping the magnetic stirring resulted in a very fast settling (a few seconds) to obtain two separated layers. Samples of the upper layer (product layer) were taken. The samples were analysed by GC (area %) in order to check the progress of the reaction. The results are shown in FIG. 5.

The data show that the reaction rate of the esterification reaction can be increased by decreasing the water concentration (compare mixture 1 vs. 2 and mixture 3 vs. 4). The data further show that the reaction rate can be increased by using an excess of HCl (compare mixture 1 vs. 3 and mixture 2 vs. 4).

Equilibrium was reached in about 4 hours in experiment 4. It is expected that by increasing temperature, a residence time of less than one or two hours can be achieved. A residence time in this range would allow for a continuous process.

EXAMPLE 3

Esterification of Succinic Acid with Methanol

General Procedure

Reaction vessels were charged with succinic acid, water, and optionally MgCl2, CaCl2, and/or extractant. The experiments are summarised in table 3 below.

The reactions in glass vessels were carried out at 80° C. for 24 hours. The reactions in an autoclave were carried out at 120° C. for 7 hours.

TABLE 3

| Exp. No. | MgCl$_2$ | CaCl$_2$ | T (° C.) | Solvent | Procedure |
|---|---|---|---|---|---|
| 1 | − | − | 80 | — | glass |
| 2 | − | − | 80 | MIBK | glass |
| 3 | + | − | 80 | — | glass |
| 4 | + | − | 80 | MIBK | glass |
| 5 | − | − | 120 | MIBK | autoclave |
| 6 | − | + | 120 | MIBK | autoclave |
| 7 | + | − | 120 | MIBK | autoclave |

Of the experiments in the table, Experiments 1, 2 and 5 are comparative in that no chloride salt was present.

For all experiments, the molar ratio of succinic acid to methanol was 1:4. The molar ratio of succinic acid to chloride salt (if used) was 1:1. The volume ratio of the organic phase and the aqueous phase at the start of the reaction was 1:1. The initial concentration of succinic acid in the aqueous phase (excluding methanol and MIBK) was 14 wt. % in all experiments.

At t=0 methanol was added. After methanol addition the temperature recovered to the reaction temperature within a few minutes. Magnetic stirring was applied at such a rate that in case of a two-phase system a finely divided emulsion was formed, to prevent mixing to be a limiting factor.

At specific times samples were taken for analysis. The mixture was allowed to settle in case of a two-phase system. Then four drops (about 0.05 ml) of the mixture or upper layer were diluted in 1.5 ml of butanol as solvent. Samples were analysed by GLC (area %). No response factors were applied, so the results are semi-quantitative.

The results are presented in FIGS. 6, 7, 8, and 9.

Figure 6:
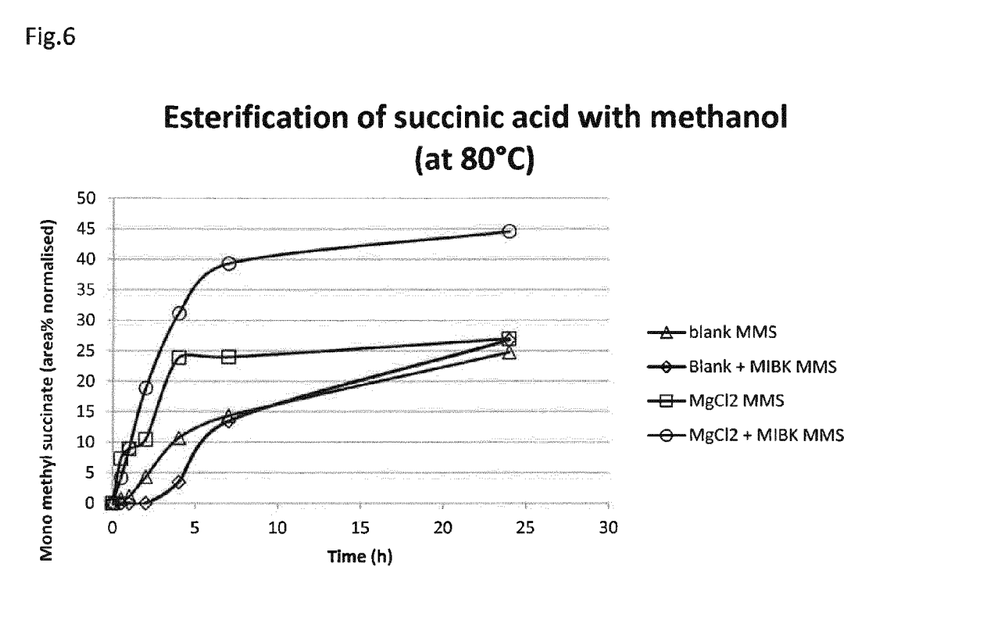

FIG. 6 shows the formation of monomethyl succinate in the presence or absence of salt. It can be seen that reaction rate for the systems comprising magnesium chloride is higher than that for systems not comprising magnesium chloride (compare experiments 1 with 3, and 2 with 4).

Figure 7:
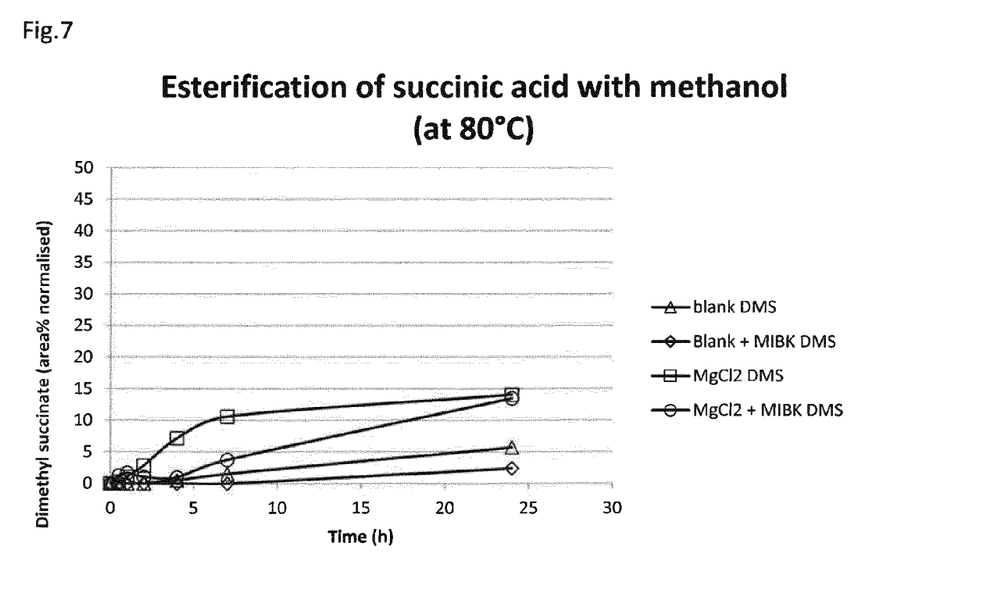

FIG. 7 shows that for dimethyl succinate formation the presence of MIBK results in a decrease in the reaction rate. Not wishing to be bound by theory it is believed that this may be caused by the monomethyl succinate being present predominantly in the MIBK phase, while the methanol is present predominantly in the aqueous phase. This shows that it may be preferred to add MIBK as extractant only at the end of the reaction. For other extractants, the situation may be different.

Figure 8:
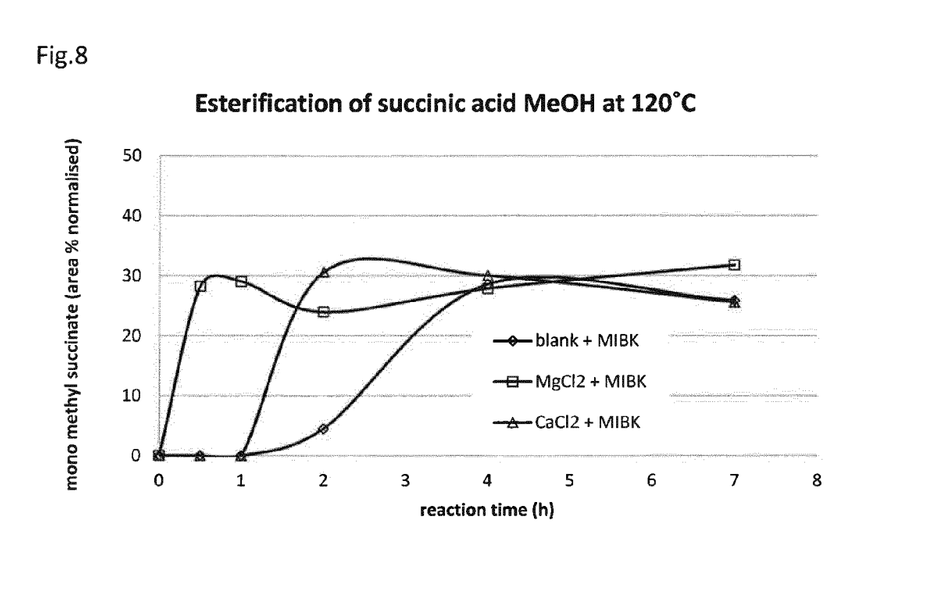

FIG. 8 shows that systems comprising calcium chloride or magnesium chloride show a higher reaction rate for the production of monomethyl succinate than the system not containing salt.

Figure 9:
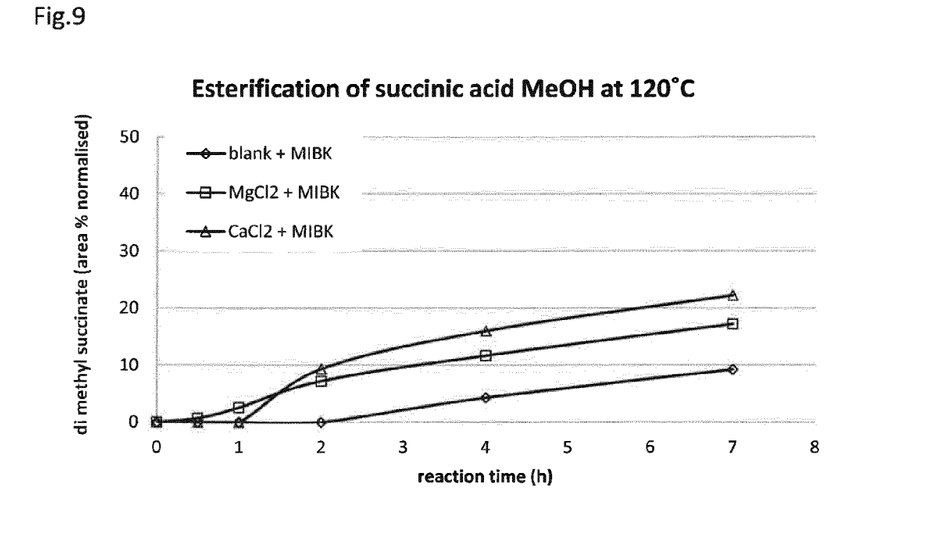

FIG. 9 shows the formation of dimethyl succinate in the presence of absence of chloride salts. Again, the system not containing salt shows the lowest reaction rate.

The invention claimed is:

1. A process for preparing a succinic acid ester comprising the steps of bringing an aqueous liquid comprising succinic acid, alcohol, and at least 5 wt. % of a dissolved chloride salt selected from magnesium chloride, calcium chloride, and zinc chloride, calculated on the weight of the liquid, to reaction conditions, thereby obtaining a succinic acid ester, and recovering the succinic acid ester and an aqueous solution comprising the dissolved chloride salt.

2. Process according to claim 1, wherein the dissolved chloride salt is magnesium chloride.

3. Process according to claim 1, wherein the dissolved chloride salt is present in an amount of at least 10 wt. %, in particular in an amount of at least 20 wt. %.

4. Process according to claim 1, wherein the step of recovering the succinic acid ester comprises a liquid-liquid separation step wherein an organic phase comprising the succinic acid ester is separated from an aqueous solution comprising a chloride salt.

5. Process according to claim 4, wherein an extractant is present during the separation step.

6. Process according to claim 5, wherein the extractant is added to the reaction medium after the esterification reaction has been completed.

7. Process according to claim 4, wherein the succinic acid ester is an ester of succinic acid with an alcohol with at least two carbon atoms, in particular at least three carbon atoms, more in particular at least four carbon atoms, and wherein no extractant is present during the separation step.

8. Process according to claim 1 which further encompasses preparing the aqueous liquid comprising succinic acid, alcohol, and dissolved chloride salt by the steps of providing an aqueous liquid comprising a calcium, magnesium, or zinc salt of a succinic acid, acidifying the aqueous liquid by the addition of HCl, and adding the alcohol before, after, or simultaneous with the addition of HCl.

9. Process according to claim 8, wherein the acidification step is combined with the esterification step, and optionally the recovery step.

10. Process according to claim 1, wherein the soluble salt is magnesium chloride and the process comprises the additional step of subjecting a solution of magnesium chloride to a thermal decomposition step at a temperature of at least 300° C., thereby decomposing magnesium chloride into magnesium oxide and hydrogen chloride.

11. Process according to claim 10 wherein the hydrogen chloride is provided in an acidification step to an aqueous liquid comprising a calcium, magnesium, or zinc salt of a succinic acid and/or wherein the magnesium oxide is provided as neutralising agent to a fermentation step, either directly or after conversion into an oxide, hydroxide, or carbonate.

12. Process according to claim 10 which additionally comprises a fermentation step wherein a carbon source is fermented by means of a micro-organism in a fermentation broth to form succinic acid and neutralizing at least part of the succinic acid by adding a base selected from an oxide, hydroxide, or carbonate of zinc, magnesium, or calcium, thereby obtaining a zinc-, magnesium-, or calcium carboxylate.

13. Process according to claim 1, wherein the succinic acid ester is a C1-C8 ester of succinic acid, in particular a C1-C4 ester, more in particular dimethyl succinate, diethyl succinate, or dibutyl succinate.

14. Process according to claim 1, which comprises the further step of reacting the succinic acid ester with hydrogen in the presence of a catalyst to form 1,4-butane diol.

* * * * *